United States Patent [19]
Barendregt et al.

[11] Patent Number: 5,501,878
[45] Date of Patent: Mar. 26, 1996

[54] PROCESS FOR REDUCING THE CARBONIZATION OF HEAT EXCHANGE SURFACES

[75] Inventors: Simon Barendregt, VR Rhoon, Netherlands; Gerhard Zimmermann; Grete Bach, both of Leipzig, Germany

[73] Assignees: Mannesmann Aktiengesellschaft, Dusseldorf, Germany; KTI Group B.V., Zoetermeer, Netherlands

[21] Appl. No.: 320,875

[22] Filed: Oct. 11, 1994

[30] Foreign Application Priority Data

Oct. 8, 1993 [DE] Germany .......................... 43 34 827.0

[51] Int. Cl.⁶ .................. B05D 3/02; B05D 3/04
[52] U.S. Cl. .................. 427/377; 134/2; 134/20; 134/39; 165/2
[58] Field of Search .................. 134/20, 39, 2; 165/2; 201/2, 39; 208/48 R; 427/377, 378; 432/2

[56] References Cited

U.S. PATENT DOCUMENTS 3,532,542 10/1970 Shimizu et al. .......................... 134/20
4,376,694 3/1983 Lohr et al. .......................... 208/48 R Primary Examiner—Michael Lusignan
Attorney, Agent, or Firm—Cohen, Pontani, Lieberman, Pavane

[57] ABSTRACT

A process for reducing the carbonization of the heat exchange surfaces in a tubular heat exchanger of boiler steel which, in particular, within a unit for the thermal cracking of hydrocarbons to alkenes and while producing steam, carries out the rapid cooling of the cracking products after they leave the cracking furnace. After the tubular heat exchanger is cleaned and before it is returned to service, the sides of the heat exchange surfaces which come into contact with the cracking products are treated under reducing conditions until the greatest possible reduction of the $Fe_2O_3$ on the surface to $Fe_3O_4$ has taken place, without submicron Fe powder being formed.

9 Claims, 1 Drawing Sheet

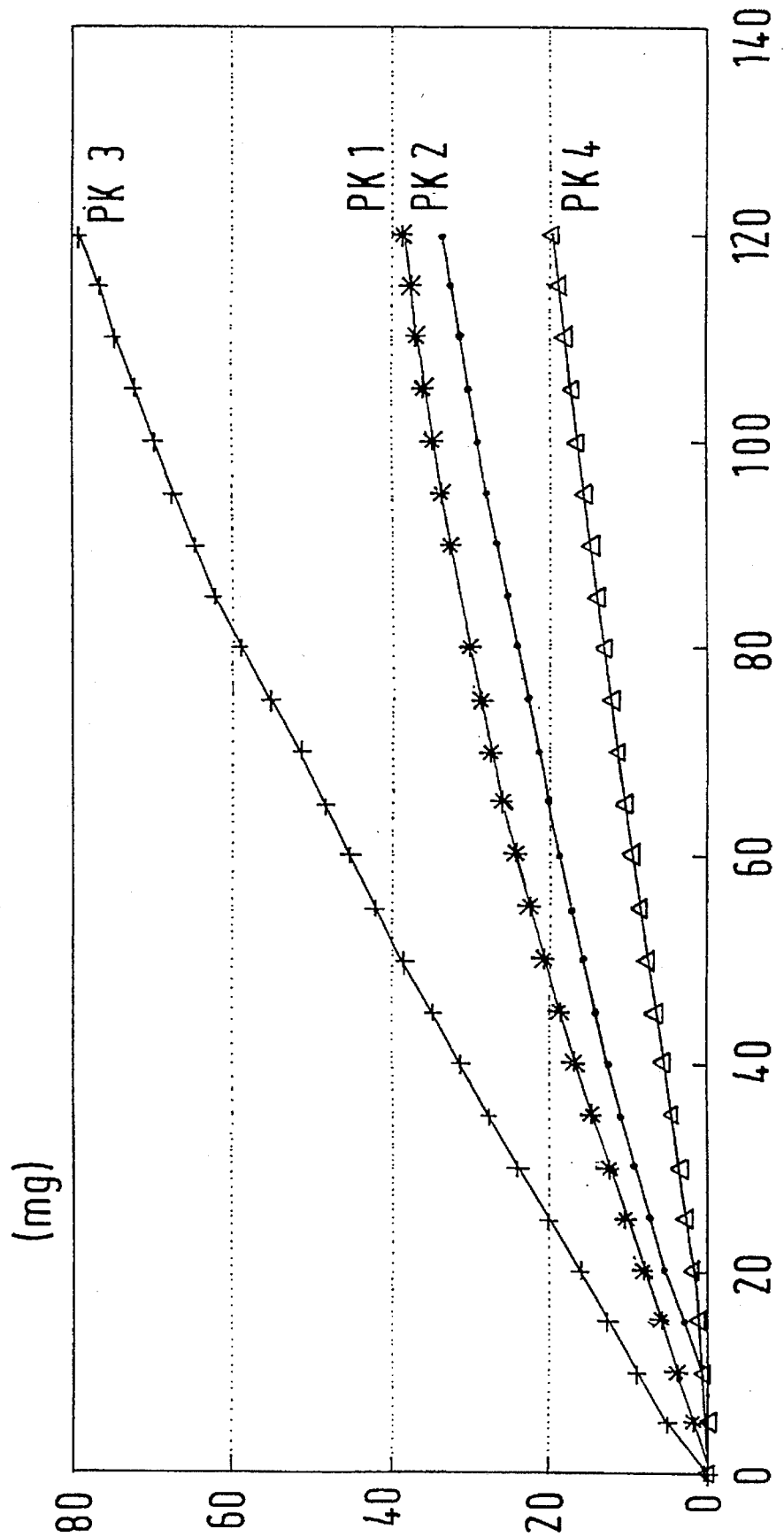

PROCESS FOR REDUCING THE CARBONIZATION OF HEAT EXCHANGE SURFACES

BACKGROUND OF THE INVENTION

1. Field of the Invention

The invention relates to a process for reducing the carbonization of the heat exchange surfaces in a tubular heat exchanger in a unit for thermally cracking hydrocarbons to alkenes, which tubular heat exchanger is used for rapidly cooling the cracking products leaving a cracking furnace.

2. Description of the Prior Art

In the production of, for example, the chemical starting material ethylene, higher hydrocarbons undergo thermal cracking in cracking furnaces. The resulting hot cracking products, which in this case consist largely of ethylene, are cooled after they leave the cracking furnace. For this purpose, heat exchangers are used for indirect heat exchange, and water is used as the coolant to produce usable steam. Devices of this type, constructed as tubular heat exchangers made of boiler steel, are also used in other types of chemical equipment in the cooling and heating of hydrocarbon products.

The effectiveness of a heat exchanger depends heavily on whether deposits which interfere with the transfer of heat are formed on the surfaces of the steel tube (e.g., a tube of 15Mo3) during the operation of the heat exchanger. This is regularly the case in devices in use today. After a certain period of operation, increasing carbonization is found on the side of the heat exchange surfaces which comes into contact with hydrocarbons. It is therefore necessary to repeatedly remove a given heat exchanger from operation after its performance has dropped off by a certain degree, and to subject it to an elaborate cleaning procedure. In modern units, this cleaning is often carried out by passing a mixture of hot steam and air through the heat exchanger on the carbonized side. This loosens and removes the deposits which have formed, so that a metal surface which will ensure good heat transfer from the hot cracking products to the tube walls of the heat exchanger again becomes available.

Even after an extremely thorough cleaning, however, newly formed hydrocarbon deposits appear shortly after the heat exchanger is returned to operation, so that cleaning must be carried out again after a relatively brief period of operation (e.g., after 20 to 60 days). This is undesirable from a technical as well as an economic point of view, because it interferes with steady longer-term operation, reduces efficiency in equipment use, and gives rise to frequent expenditures for the cleaning process itself. For this reason, attempts have been made for years to find solutions which would prevent the rapid carbonization of heat exchanger surfaces.

It has been suggested in EP 0 022 349 A1 that a protective film of oxides of the metals Ca, Mg, Al, Ca, Ti, Zr, Hf, Ta, Nb, or Cr be vapor-deposited on the heat exchanger surface that is subject to carbonization. This process is relatively expensive, however, and leads to only limited success.

A similar procedure, i.e., the application of a protective coating, is also suggested in EP 0 110 486 A1. In addition to metal oxides, certain metals, aluminates and silicates are to be used for this purpose. Although this solution also yields improvements, it cannot be considered satisfactory in every case.

Another improvement that is not adequate in every case results from a coating based on silicone resin that is known from NL 84 01 804 Al, in which coating silicon carbide, boron carbide, titanium carbide, silicon nitride or boron nitride is introduced into the resin.

Finally, reference should be made to the attempted use of molybdenum-free steel alloys for the heat exchanger robes. It was once believed that the molybdenum contained in the usual heat exchanger steels had a catalytic effect which promoted carbonization. However, this did not prove to be the case.

The previously suggested solutions have in common the fact that, practically speaking, they are applicable only to new equipment, not to equipment already in operation (except in the case of revamping).

SUMMARY OF THE INVENTION

It is thus an object of the invention to provide a process that can significantly reduce the carbonization which until now has occurred during the operation of the heat exchangers in question.

Pursuant to this object, and others which will become apparent hereafter, one aspect of the present invention resides in treating the sides of the heat exchange surfaces, after cleaning, which come into contact with the cracking products under reducing conditions until a greater reduction of $Fe_2O_3$ on the surface to $Fe_3O_4$ occurs, without forming submicron Fe powder.

The invention is based on the surprising discovery that a certain form of iron oxide, namely $Fe_2O_3$, has a very strong catalytic effect on carbonization, while another form of iron oxide, $Fe_3O_4$, has practically no such catalytic effect. The metallic iron in a composite of metallic materials displays only mid-level activity, whereas the superfine, powder-form iron particles which remain on the inner surface of heat exchanger tubes in a finely distributed fashion after decarbonization result in a very high level of carbon formation when they are present in reduced form. The determinant factor in the consistently observed rapid carbonization of the heat exchanger surfaces is therefore the $Fe_2O_3$. Unfortunately, this oxide is formed on the steel tube surfaces during the standard cleaning procedure using a hot steam/air mixture. As a result, it is just such freshly cleaned surfaces which display a particularly high carbonization rate in the initial phase after the heat exchanger is put back into operation, i.e., these surfaces rapidly acquire a certain hydrocarbon coating. Subsequently, the carbonization rate drops, because the hydrocarbon coating serves as a protective film. A similar negative effect is produced by the finely distributed iron clusters which are incorporated into the carbon matrix during carbonization and released during decarbonization. These clusters can also lead to high initial carbonization of the heat exchanger.

In order to specifically prevent this rapid new formation of an initial carbon coating on the heat exchanger surface, the invention calls for an additional treatment to be carried out, after the heat exchanger is cleaned and before it is put back into operation, on the surface parts which come into contact with cracking products. This treatment reduces the catalytically active $Fe_2O_3$ to the inactive $Fe_3O_4$, while the reduction of Fe clusters from the carbon matrix to metallic Fe particles (submicron Fe powder) is avoided. Usefully, this is done after the cleaning procedure (which can be carried out as usual, for instance, with a hot steam/air mixture) by passing a mixture of hot steam and hydrogen through the heat exchanger in such a composition that on the inner surface of the heat exchanger, which is exposed to carbonization during pyrolysis, the $Fe_2O_3$ is deliberately converted by a reducing atmosphere to $Fe_3O_4$, but no thoroughgoing reduction of the iron oxides to Fe particles occurs. After sufficient conversion has taken place, the heat exchanger can be placed back into service. Because there is no longer a high level of catalytic activity by $Fe_2O_3$ on the surface, new carbonization begins only after a very considerable time lag. This relatively simple extra treatment following the standard cleaning process permits the operating periods of the heat exchanger to be lengthened significantly. An essential point here is that no structural changes are made in the heat exchanger itself and the process can also be used for already existing equipment. Furthermore, no coatings of any sort, which might interfere with the transfer of heat, are necessary.

It has proved advantageous for the mixture of steam and hydrogen to pass through the heat exchanger at the usual operating temperature of a TLE unit, i.e., approximately 400° to 500° C., and for the treatment to last from 1 to 6 hours. Usefully, the share of hydrogen in the mixture is 5 to 20 percent by weight; and preferably, it is 5 to 10 percent by weight. The pressure of the mixture passed through the heat exchanger can correspond to the usual operating pressure of a TLE unit, e.g., approximately 0.5 to 20 bar, with a preferred range of 1.5 to 2.5 bar.

BRIEF DESCRIPTION OF THE DRAWING

In what follows, the invention is described in greater detail in reference to a number of comparative examples and executed examples according to the invention. The drawing shows the formation of carbon on a heat exchange surface as a function of various aftertreatments following decarbonization.

EXAMPLE 1

(Comparative Example)

In laboratory pyrolysis equipment of quartz (vertical tube with dimensions of 500× 20×1 mm, $V_{tube}=127$ cm³, electrically heated and regulated), technical propane (composition: propane 95.0% by weight; propylene 2:3% by weight; isobutane 2.5% by weight; ethane 0.2% by weight) was subjected to pyrolysis under normal pressure at a temperature of 820° C. and a holding time of 0.3 seconds with nitrogen as the dilutant. The propane flow rate was 6 l/h; the nitrogen flow rate was 5 l/h. Under these conditions, the propane conversion was 95%, and the ethylene/propylene weight ratio in the cracked gas was 2.1.

In a tubular segment of the same dimensions which was attached to the pyrolysis zone, a separate heating element simulated the temperature of the cracked gas cooler, which could be set as desired in the range from 350° to 500° C. In this tubular section, a sensor of standard TLE material (15Mo3) measuring 20×7×1 mm was hung on a platinum wire attached to the balance arm of an electrothermal scale and positioned in the post-cracking zone. In this way, the change in sensor weight resulting from carbon formation could be continuously observed and measured. At 500° C., the rate of carbon formation on the sensor rose within 10 minutes after the experiment started from an initial rate ($r_c(0)$) of 15 µg/min (measured 5 minutes into the experiment) to a maximum rate ($r_c(max)$) of 258 µg/min. Over the course of 2 more hours, a quasi-stationary value of $r_c(stat)=$ 65 µg/min was established. In the pyrolysis cycle which followed decarbonization with air (5 l/h), both the maximum carbon formation rate $r_c(max)$ and the quasi-stationary carbon formation rate $r_c(stat)$ rose sharply. This trend continued during additional pyrolysis-decarbonization cycles, as shown in Table 1.

TABLE 1

| Cycle | $r_c(0)$ [µg/min] | $r_c(max)$ [µg/min] | $r_c(stat)$ [µg/min] |
|---|---|---|---|
| 1 | 15 | 258 | 65 |
| 2 | 340 | 465 | 220 |
| 3 | 445 | 485 | 283 |
| 4 | 510 | 648 | 340 |
| 5 | 835 | 1043 | 530 |

EXAMPLE 2

(Comparative Example)

In the same equipment as that used in Example 1 and under analogous external conditions, technical propane was subjected to pyrolysis and the formation of carbon on 15Mo3 sensors of analogous size was observed in the post-cracking zone at 500° C. In contrast to Example 1, decarbonization was carried out using a mixture of air and steam (air flow rate and steam flow rate: 6 l/h each).

During the pyrolysis which followed, the initial rate of carbon formation was $r_c(0)=0$. The rate increased rapidly to $r_c(max)=480$ µg/min. Two hours later, a quasistationary value for $r_c(stat)$ of 245 µg/min was measured. Both of these values are greater than the corresponding values in Example 1.

EXAMPLE 3

(Comparative Example)

In the same equipment as that used in Example 1 and under analogous external conditions, technical propane was subjected to pyrolysis and the formation of carbon on 15Mo3 sensors of analogous size was observed in the post-cracking zone at 500° C.

In contrast to Example 1, the sensor underwent a four-hour after-treatment with steam following pyrolysis and air decarbonization; the steam flow rate was 17 l/h. During the pyrolysis of propane which followed, a value of 0 was measured for $r_c(0)$. After this, the rate of carbon formation rose quickly to $r_c(max)=520$ µg/min, while the value of $r_c(stat)$ was 330 µg/min. Both of these values are greater than the corresponding values in Example 1.

EXAMPLE 4

(Comparative Example)

In the same equipment as that used in Example 1 and under analogous external conditions, technical propane was subjected to pyrolysis and the formation of carbon on 15Mo3 sensors of analogous size was observed in the post-cracking zone at 500° C.

In contrast to Examples 1 and 2, the sensor was subjected after pyrolysis and air decarbonization to an after-treatment with pure hydrogen (flow rate: 5 l/h, duration of treatment: 4 h). During the pyrolysis which followed, a very high value of $r_c(0)=r_c(max)=1050$ µg/min was measured for carbon formation in the post-cracking zone, more than twice as high as in the course of reaction according to Example 1. Similarly, the value of $r_c(stat)=420$ µg/min is also much higher than the corresponding value in Example 1.

EXAMPLE 5

(Example according to the Invention)

In the same equipment as that used as in Example 1 and under analogous external conditions, technical propane was subjected to pyrolysis and the formation of carbon on 15Mo3 sensors of analogous size was observed in the post-cracking zone at 500° C.

In contrast to the comparative examples described above, the sensor was subjected following pyrolysis and air decarbonization to a four-hour after-treatment with a mixture of hydrogen and steam; the overall flow rate was uniformly 10 l/h and the volume ratio of $H_2/H_2O$ was changed from 9 to 0.1.

The results of the experiments are summarized in Table 2.

TABLE 2

| Vol. Ratio $H_2/H_2O$ | $r_c$ (0) [µg/min] | $r_c$ (max) [µg/min] | $r_c$ (stat) [µg/min] |
|---|---|---|---|
| no after-treatment | 340 | 465 | 200 |
| 9 | 1 150 | 1 150 | 500 |
| 4 | 470 | 470 | 180 |
| 2.5 | 110 | 410 | 180 |
| 1.5 | 35 | 310 | 170 |
| 0.7 | 0 | 345 | 160 |
| 0.1 | 0 | 500 | 520 |

It is evident that even at a volume ratio of 2.5 for $H_2/H_2O$, the after-treatment according to the invention reduces the formation of carbon in the post-cracking zone at the beginning of the pyrolysis process to less than 1/3 of the level obtained without after-treatment. When the proportion of $H_2$ is reduced further, the formation of carbon at the start of the experiment is suppressed completely; the values achieved for $r_c$(max) and $r_c$(stat) are lower than those achieved without after-treatment or with mixtures rich in $H_2$. At very low proportions of hydrogen, carbon formation increases again.

EXAMPLE 6

(Example according to the Invention)

In the same equipment as that used in Example 1 and under analogous external conditions, technical propane was subjected to pyrolysis and the formation of carbon on 15Mo3 sensors of analogous size was observed in the post-cracking zone at 500° C.

The after-treatment was carried out with a mixture of 5 /h hydrogen and 8.7 l/h steam (volume ratio of $H_2/H_2O$=0.6), and the duration of treatment varied between 1 and 12 hours. Table 3 shows the rate of carbon formation on the after-treated sensors compared to those measured without after-treatment during the second pyrolysis cycle.

The variations in after-treatment duration showed that, in all cases, there was no formation of carbon at the start of the subsequent pyrolysis experiment ($r_c$(0)=0), whereas without after-treatment the rate of carbon formation was 340 µg/min even at the start of the experiment. However, Table 3 also shows that carbon formation increases again in the case of very prolonged after-treatment.

TABLE 3

| After-treatment [h] | $r_c$ (0) [µg/min] | $r_c$ (max) [µg/min] | $r_c$ (stat) [µg/min] |
|---|---|---|---|
| no after-treatment | 340 | 465 | 200 |
| 1 | 0 | 370 | 155 |

TABLE 3-continued

| After-treatment [h] | $r_c$ (0) [µg/min] | $r_c$ (max) [µg/min] | $r_c$ (stat) [µg/min] |
|---|---|---|---|
| 6 | 0 | 195 | 140 |
| 12 | 0 | 295 | 160 |

EXAMPLE 7

(Comparison and Invention)

In laboratory pyrolysis equipment as in Example 1, four sensors (Sensors 1–4) of 15Mo3 were carbonized in the same way using technical propane. After this, each of the individual sensors was subjected to a different treatment procedure, as follows:

| | |
|---|---|
| Sensor 1 | Decarbonization with air (5 l/h) |
| Sensor 2 | Decarbonization with air (5 l/h) and steam (6 l/h) |
| Sensor 3 | Decarbonization with air (5 l/h) and subsequent treatment with steam (17 l/h; 4 h) |
| Sensor 4 | Decarbonization with air (5 l/h) and subsequent treatment for a duration of 6 hours with a mixture of steam (5 l/h) and water (7 l/h). |

Thus only Sensor 4 was treated in accordance with the invention. All four sensors were again subjected to carbonization with technical propane (conditions as in Example 1) and the formation of carbon over a period of 2 hours was measured. The results are shown in the drawing in the form of a graph. A comparison reveals that by far the lowest rams of carbon formation were measured on Sensor 4, which was treated in accordance with the invention. The total quantities of carbon measured (Sensor 1: $Q_c$=40.5 mg; Sensor 2: $Q_c$=38.2 mg; Sensor 3: $Q_c$=76.3 mg; Sensor 4: $Q_c$=24.1 mg) indicate that the treatment according to the invention permits running time to be lengthened significantly in comparison to that possible during operation without $H_2/H_2O$ treatment (in the given example, by approximately 40%).

The invention is not limited by the embodiments described above which are presented as examples only but can be modified in various ways within the scope of protection defined by the appended patent claims.

We claim:

1. A process for reducing carbonization of heat exchange surfaces in a tubular heat exchanger for a rapid cooling of cracking products leaving a cracking furnace, comprising the steps of: cleaning the tubular heat exchanger; and, treating heat exchange surfaces which come into contact with the cracking products under conditions which reduce $Fe_2O_3$ on the surfaces to $Fe_3O_4$ to a greatest possible extent, without forming submicron Fe powder.

2. A process as defined in claim 1, wherein the treating step includes passing a mixture of hot steam and hydrogen through the tubular heat exchanger on a side which comes into contact with the cracking products.

3. A process as defined in claim 2, wherein the steam/hydrogen mixture has a temperature in a range between 400° and 550° C.

4. A process as defined in claim 2, including subjecting the heat exchange surface to the steam/hydrogen mixture for a duration of between 1 and 6 hours.

5. A process as defined in claim 2, including passing a steam/hydrogen mixture having a hydrogen connect between 5 and 20% by weight through the tubular heat exchanger.

6. A process as defined in claim 5, wherein the hydrogen content of the steam/hydrogen mixture is between 5 and 10% by weight.

7. A process as defined in claim 2, including passing the steam/hydrogen mixture through the tubular heat exchanger under a pressure of between 0.5 and 20 bar.

8. A process as defined in claim 7, including passing the steam/hydrogen mixture through the tubular heat exchanger under a pressure of between 1.5 and 2.5 bar.

9. A process as defined in claim 2, wherein the cleaning step includes cleaning with a hot steam/air mixture.

* * * * *